US011707731B2

(12) United States Patent
Colijn et al.

(10) Patent No.: US 11,707,731 B2
(45) Date of Patent: Jul. 25, 2023

(54) MOLYBDENUM-VANADIUM-NIOBIUM-CERIA-BASED CATALYST FOR OXIDATIVE DEHYDROGENATION OF ALKANES AND/OR ALKENE OXIDATION (71) Applicant: SHELL OIL COMPANY, Houston, TX (US)

(72) Inventors: Hendrik Albertus Colijn, Amsterdam (NL); Michael Johannes Franciscus Maria Verhaak, Amsterdam (NL)

(73) Assignee: SHELL USA, INC., Houston, TX (US)

( * ) Notice: Subject to any disclaimer, the term of this patent is extended or adjusted under 35 U.S.C. 154(b) by 1096 days.

(21) Appl. No.: 16/319,035

(22) PCT Filed: Jul. 20, 2017

(86) PCT No.: PCT/EP2017/068324
§ 371 (c)(1),
(2) Date: Jan. 18, 2019

(87) PCT Pub. No.: WO2018/015479
PCT Pub. Date: Jan. 25, 2018

(65) Prior Publication Data
US 2021/0346869 A1 Nov. 11, 2021

(30) Foreign Application Priority Data
Jul. 22, 2016 (EP) .................................... 16180818

(51) Int. Cl.
B01J 23/28 (2006.01)
B01J 23/10 (2006.01)
B01J 35/00 (2006.01)
B01J 35/02 (2006.01)
B01J 37/02 (2006.01)
C07C 5/48 (2006.01)
B01J 23/22 (2006.01)
B01J 27/057 (2006.01)
C07C 51/25 (2006.01)
B01J 23/20 (2006.01)
C07C 51/21 (2006.01)
B01J 23/16 (2006.01)

(52) U.S. Cl.
CPC ............ B01J 23/28 (2013.01); B01J 23/10 (2013.01); B01J 23/16 (2013.01); B01J 23/20 (2013.01); B01J 23/22 (2013.01); B01J 27/057 (2013.01); B01J 35/0013 (2013.01); B01J 35/0033 (2013.01); B01J 35/023 (2013.01); B01J 35/026 (2013.01); B01J 37/0221 (2013.01); C07C 5/48 (2013.01); C07C 51/21 (2013.01); C07C 51/252 (2013.01); B01J 2523/3712 (2013.01); B01J 2523/56 (2013.01); B01J 2523/64 (2013.01); B01J 2523/68 (2013.01); C07C 2523/10 (2013.01); C07C 2523/28 (2013.01); C07C 2527/057 (2013.01)

(58) Field of Classification Search
CPC ... B01J 23/28; B01J 23/16; B01J 23/10; B01J 23/22; B01J 23/20; B01J 27/057; B01J 27/0576; B01J 37/0009; B01J 37/04; B01J 37/0221; B01J 35/0013; B01J 35/0033; B01J 35/023; B01J 35/026; B01J 2523/3712; B01J 2523/56; B01J 2523/64; B01J 2523/68; B01J 2523/00; C07C 2523/10; C07C 2523/16; C07C 2523/20; C07C 2523/22; C07C 2523/28; C07C 2527/057; C07C 2527/02; C07C 2527/19; C07C 2527/195; C07C 2527/198; C07C 2527/199; C07C 5/48; C07C 51/21; C07C 51/25; C07C 51/252
USPC .............. 502/304, 305, 311, 312, 321, 353; 585/252, 520, 616, 617, 627, 624, 621, 585/630, 654, 658, 662, 663
See application file for complete search history.

(56) References Cited
U.S. PATENT DOCUMENTS
7,091,377 B2 8/2006 Borgmeier et al.
2004/0147393 A1 7/2004 Hibst et al.
(Continued)

FOREIGN PATENT DOCUMENTS
CN 102989487 A 3/2013
CN 104941668 A 9/2015
(Continued)

OTHER PUBLICATIONS

Machine Translation of CN 104941668 A, 2015.*
(Continued)

Primary Examiner — Elizabeth D Wood
(74) Attorney, Agent, or Firm — Shell USA, Inc.

(57) ABSTRACT

The invention relates to a catalyst which comprises: a) a mixed metal oxide of molybdenum, vanadium, niobium and optionally tellurium; and b) ceria particles having a crystallite size greater than 15 nanometers (nm); wherein the amount of the ceria particles, based on the total amount of the catalyst, is of from 1 to 60 wt. %. Further, the invention relates to a process for preparing a catalyst, which comprises mixing a mixed metal oxide of molybdenum, vanadium, niobium and optionally tellurium with ceria particles having a crystallite size greater than 15 nanometers (nm), wherein the amount of the ceria particles, based on the total amount of the catalyst, is of from 1 to 60 wt. %. Still further, the invention relates to an alkane oxidative dehydrogenation and/or alkene oxidation process wherein such catalyst is used.

8 Claims, 3 Drawing Sheets (56) References Cited

U.S. PATENT DOCUMENTS

| | | |
|---|---|---|
| 2004/0256288 A1 | 12/2004 | Font Freide |
| 2007/0105228 A1* | 5/2007 | Vanderspurt ............. B01J 35/10 436/55 |
| 2010/0256432 A1 | 10/2010 | Arnold et al. |

FOREIGN PATENT DOCUMENTS

| | | |
|---|---|---|
| EP | 2687577 A1 | 1/2014 |
| WO | 0011113 A1 | 3/2000 |
| WO | 03064035 A1 | 8/2003 |
| WO | 2007009951 A1 | 1/2007 |
| WO | 2010096909 A1 | 9/2010 |

OTHER PUBLICATIONS

International Search Report and Written Opinion received for PCT Patent Application No. PCT/EP2017/068324, dated Oct. 24, 2017, 14 pages.

Chu et al., "A Self-Redox Pure-Phase M1 MovnbteOx/CeO2 Nanocomposite as a Highly Active Catalyst for Oxidative Dehydrogenation of Ethane" Journal of Catalysis, vol. 329, Jul. 12, 2015, pp. 471-478, XP055326810.

Scardi et al., "Microstructural Properties: Lattice Defects and Domain Size Effects", Powder diffraction: theory and practice, 2008, Chapter 13, pp. 376-413.

* cited by examiner

MOLYBDENUM-VANADIUM-NIOBIUM-CERIA-BASED CATALYST FOR OXIDATIVE DEHYDROGENATION OF ALKANES AND/OR ALKENE OXIDATION

CROSS REFERENCE TO RELATED APPLICATIONS

This is a national stage application of International Application No. PCT/EP2017/068324, filed 20 Jul. 2017, which claims benefit of priority to European Patent Application No. 16180818.3, filed 22 Jul. 2016.

FIELD OF THE INVENTION

The present invention relates to a catalyst suitable to be used in a process of alkane oxidative dehydrogenation (oxydehydrogenation; ODH) and/or alkene oxidation; to a process for preparing such catalyst; and to an alkane ODH and/or alkene oxidation process wherein such catalyst is used.

BACKGROUND OF THE INVENTION

It is known to oxidatively dehydrogenate alkanes, such as alkanes containing 2 to 6 carbon atoms, for example ethane or propane resulting in ethylene and propylene, respectively, in an oxidative dehydrogenation (oxydehydrogenation; ODH) process. Examples of alkane ODH processes, including catalysts and other process conditions, are for example disclosed in U.S. Pat. No. 7,091,377, WO2003064035, US20040147393, WO2010096909 and US20100256432. Mixed metal oxide catalysts containing molybdenum (Mo), vanadium (V), niobium (Nb) and optionally tellurium (Te) as the metals, can be used as such oxydehydrogenation catalysts. Such catalysts may also be used in the direct oxidation of alkenes to carboxylic acids, such as in the oxidation of alkenes containing 2 to 6 carbon atoms, for example ethylene or propylene resulting in acetic acid and acrylic acid, respectively.

In particular, a catalyst comprising both $MoVNbTeO_x$ mixed metal oxide and ceria (cerium(IV) oxide; $CeO_2$) is disclosed by Chu et al. in "A self-redox pure-phase M1 $MoVNbTeO_x/CeO_2$ nanocomposite as a highly active catalyst for oxidative dehydrogenation of ethane", Journal of Catalysis, 329, 2015, pages 471-478. According to said article, $MoVNbTeO_x$ mixed metal oxide/$CeO_2$ nanocomposites with different $CeO_2$ particle sizes may be formed by a physical mixing method and a sol-gel method. The particle size of the $CeO_2$ particles in the final catalysts were 19.1 nm (physical mixing) and 4.4 nm (sol-gel method). Further, the mixed metal oxide particles in the final catalysts had an average width of 107-108 nm and an average length of 215-216 nm.

Further, in Chinese patent application CN104941668, whose inventors are also authors of the above-mentioned article, a $MoVNbTeO_x$ mixed metal oxide containing catalyst additionally comprising 5 to 20 wt. % of ceria ($CeO_2$) particles having a particle size of from 2 to 30 nm is disclosed.

Still further, in addition to a sol-gel process, said CN104941668 discloses a physical mixing process as a method for preparing such catalyst which comprises the following steps. In a $1^{st}$ step, a cerium oxide sol in water is formed. In a $2^{nd}$ step, said sol is oven dried and ground to obtain a cerium oxide powder. Preferably, the sol is oven dried at a temperature of 100 to 130° C. for 2 to 5 hours and the ground powder has a particle size of 80-120 meshes. 80-120 U.S. mesh corresponds to 125-177 micrometers. In a $3^{rd}$ step, said cerium oxide powder and a $MoVNbTeO_x$ mixed metal oxide are mixed, preferably by means of grinding for 10 to 20 minutes. In a $4^{th}$ step, the obtained mixture is baked at 300 to 600° C. for 3 to 6 hours to obtain the catalyst wherein the ceria particles have a particle size of from 10 to 30 nm.

In Examples 1, 3 and 5 of CN104941668, the physical mixing process was applied. In said Examples 1, 3 and 5, the ceria particle size in the final catalysts was 20 nm, 15 nm and 20 nm, respectively. Further, in said Examples 1, 3 and 5, for the $MoVNbTeO_x$ mixed metal oxide, the particle diameter was 75 nm, 120 nm and 90 nm, respectively, and the particle length was 225 nm, 225 nm and 180 nm, respectively. According to CN104941668, the reduced particle size of the $CeO_2$ nanoparticles promotes the progression of the solid-phase redox reaction of the nanocomposite catalyst during the calcination process, so as to enhance the catalytic activity.

It is an objective of the present invention to provide a mixed metal oxide catalyst containing Mo, V, Nb and optionally Te, which may have an increased activity and/or selectivity and/or stability in an alkane ODH and/or alkene oxidation process.

SUMMARY OF THE INVENTION

Surprisingly it was found that such mixed metal oxide catalyst containing Mo, V, Nb and optionally Te having one or more of the above-mentioned improved properties may be a catalyst, which additionally comprises ceria particles having a crystallite size greater than 15 nanometers (nm; $10^{-9}$ meters).

Accordingly, the present invention relates to a catalyst which comprises:

a) a mixed metal oxide of molybdenum, vanadium, niobium and optionally tellurium; and b) ceria particles having a crystallite size greater than 15 nanometers (nm);

wherein the amount of the ceria particles, based on the total amount of the catalyst, is of from 1 to 60 wt. %.

Further, the present invention relates to a process for preparing such catalyst, which comprises mixing a mixed metal oxide of molybdenum, vanadium, niobium and optionally tellurium with ceria particles having a crystallite size greater than 15 nanometers (nm), wherein the amount of the ceria particles, based on the total amount of the catalyst, is of from 1 to 60 wt. %.

Still further, the present invention relates to an alkane ODH and/or alkene oxidation process wherein such catalyst is used.

DETAILED DESCRIPTION OF THE INVENTION

While the catalyst and processes of the present invention and the stream or streams used in said processes are described in terms of "comprising", "containing" or "including" one or more various described steps or components, they can also "consist essentially of" or "consist of" said one or more various described steps or components.

In the context of the present invention, in a case where a stream or catalyst comprises two or more components, these components are to be selected in an overall amount not to exceed 100 vol. % or 100 wt. %.

The present catalyst comprises two components. A first component a) comprises a mixed metal oxide of molybdenum, vanadium, niobium and optionally tellurium. A second component b) comprises ceria particles having a crystallite size which is greater than 15 nm.

Suitably, in the present invention, the ceria in the above-mentioned component b) comprises cubic ceria. Cubic ceria means that the ceria crystallizes in a cubic space group. In particular, cubic ceria crystallizes in a face-centered cubic space group, more in particular in the face-centered cubic space group $Fm\bar{3}m$. Said space group $Fm\bar{3}m$ is in so-called Hermann-Mauguin notation and corresponds to the "225" space group in the International Tables for Crystallography, Volume A. "Cubic" refers to a crystal system where the atomic stacking displays a combination of internal symmetry elements that results in a cube-shaped unit cell. For $CeO_2$, the cubic cell edge length typically lies in the range 5.2-5.4 Å under ambient temperature and pressure.

Thus, in the present invention, the ceria particles as contained in the catalyst have a crystallite size which is greater than 15 nm. Unless indicated otherwise, within the present specification, by "crystallite size" reference is made to an average crystallite size (volume-based, average crystallite size).

Crystallites, also referred to as crystalline domains, are coherently scattering regions within a crystalline material. See for example Paolo Scardi, "Microstructural properties: lattice defects and domain size effects" in "Powder diffraction: theory and practice", R. E. Dinnebier (ed.) & S. J. L. Billinge (ed.), RSC Publishing, Cambridge, UK, 2008. Crystallite sizes can be determined by X-ray diffraction. In particular, the crystallite size can be derived from the broadening of the reflections measured with X-ray diffraction. Preferably, in the present invention, the crystallite size is an approximated crystallite size as determined by X-ray diffraction using the following, so-called "Scherrer equation"

$$\tau = (K\lambda)/(\beta \cos \theta)$$

where:

$\tau$ is the average (volume-based) crystallite size [in nm];

$K=1.0$, wherein K is a dimensionless factor which takes into account crystal shape, reflection indices, reflection shape and size distribution;

$\lambda$ is the X-ray wavelength [in nm];

$\beta$ is the reflection width [in rad] at half the maximum intensity, after subtracting the instrumental broadening; and $\cos \theta$ is the cosine of the Bragg angle.

Suitably, when determining the crystallite size on the basis of the above-described "Scherrer equation", all non-instrumental broadening is assigned to domain size effects and other effects like micro-strain are ignored. Further, the crystallite size is determined under ambient temperature and pressure.

The ceria particles as contained in the catalyst of the present invention have a crystallite size which is greater than 15 nm, preferably greater than 30 nm. Preferably, the crystallite size of the ceria particles as contained in the catalyst is of from greater than 15 nm to 1,000 nm, more preferably of from greater than 30 nm to 500 nm, more preferably of from 50 to 500 nm, even more preferably of from 100 to 200 nm, most preferably of from 110 to 140 nm. Preferably, the crystallite size of the ceria particles as contained in the catalyst is at least 20 nm, more preferably at least greater than 20 nm, more preferably at least 25 nm, more preferably at least 30 nm, more preferably at least greater than 30 nm, more preferably at least 35 nm, more preferably at least 40 nm, more preferably at least 50 nm, more preferably at least 60 nm, more preferably at least 70 nm, more preferably at least 80 nm, more preferably at least 90 nm, more preferably at least 100 nm, most preferably at least 110 nm. Preferably, the crystallite size of the ceria particles as contained in the catalyst is at most 1,000 nm, more preferably at most 700 nm, more preferably at most 500 nm, more preferably at most 400 nm, more preferably at most 300 nm, more preferably at most 200 nm, more preferably at most 180 nm, more preferably at most 170 nm, more preferably at most 160 nm, more preferably at most 150 nm, more preferably at most 140 nm, most preferably at most 130 nm.

Further, in the present invention, preferably at least 70 mass %, or at least 80 mass %, or at least 90 mass %, or at least 95 mass %, or at least 99 mass % up to 100 mass % of the ceria particles as contained in the catalyst of the present invention have a crystallite size which is greater than 15 nm, more preferably greater than 30 nm, which latter crystallite size may lie in the ranges and which may have the minimums and maximums as described above for the (volume-based, average) crystallite size for the ceria particles as contained in the catalyst of the present invention.

Still further, preferably in the present invention, the ceria particles as contained in the catalyst comprise cubic ceria, in particular ceria which crystallizes in a face-centered cubic space group, more in particular in the face-centered cubic space group $Fm\bar{3}m$, and the crystallite size of the ceria particles as contained in the catalyst, as derived from the broadening of the 4 peaks in the X-ray diffraction pattern at the four (h,k,l) indices mentioned in the table below, is greater than 15 nm, more preferably greater than 30 nm, which latter crystallite size may lie in the ranges and which may have the minimums and maximums as described above for the (volume-based, average) crystallite size for the ceria particles as contained in the catalyst of the present invention. Said (h,k,l) indices are indices of the Bragg reflection from the set of parallel equidistant net planes (h,k,l), which indices are also called "Laue indices". The crystallite size may be determined using radiation of any wavelength in the X-ray wavelength region. One example is $CuK\alpha$ radiation, as exemplified in the table below with reference to $2\theta$, wherein $\theta$ is the Bragg angle from the above-described "Scherrer equation".

| (h, k, l)  | 2θ [CuKα] (°) |
|------------|---------------|
| (1, 1, 1)  | 28.5          |
| (2, 0, 0)  | 33.0          |
| (2, 2, 0)  | 47.4          |
| (3, 1, 1)  | 56.3          |

As mentioned above, by the use of ceria particles having a crystallite size greater than 15 nm, a mixed metal oxide catalyst containing Mo, V, Nb and optionally Te, is provided which may have an increased activity and/or selectivity and/or stability in an alkane ODH and/or alkene oxidation process. Further reference is made to the below-included Examples. Therefore, suitably, the present catalyst is a catalyst for alkane oxidative dehydrogenation and/or alkene oxidation.

In addition to the above-mentioned advantage(s), the use of larger ceria particles, that is to say having a crystallite size greater than 15 nm, may be advantageous in that catalysts comprising a mixed metal oxide of molybdenum, vanadium, niobium and optionally tellurium and such larger ceria particles may advantageously be manufactured easier. For the catalysts can be made on a large scale by mixing dry powders rather than using wet suspensions of particles. For example, there is advantageously no need to first make a sol of relatively small ceria particles, for example by dissolving cerium nitrate and citric acid in water to obtain a cerium oxide sol as taught by above-mentioned CN104941668. Further, generally, said larger ceria particles are cheaper. Still further, when using larger ceria particles there are less concerns in relation to HSSE issues (HSSE=Health, Safety, Security and Environment), inter alia because such larger ceria particles are less dusty and are therefore less prone to unwanted distribution via the air when making the catalyst. Yet another advantage may be that by using larger ceria particles, more especially in a case where the size of such larger ceria particles better matches the size of the mixed metal oxide particles, the mechanical strength of the final catalysts may be improved.

As mentioned above, the first component a) of the present catalyst comprises a mixed metal oxide of molybdenum, vanadium, niobium and optionally tellurium. Therefore, the present catalyst is a mixed metal oxide catalyst containing Mo, V, Nb and optionally Te.

In the present invention, the above-mentioned mixed metal oxide of molybdenum, vanadium, niobium and optionally tellurium may have the following formula:

$Mo_1V_aTe_bNb_cO_n$ wherein:

a, b, c and n represent the ratio of the molar amount of the element in question to the molar amount of molybdenum (Mo);

a (for V) is from 0.01 to 1, preferably 0.05 to 0.60, more preferably 0.10 to 0.40, more preferably 0.20 to 0.35, most preferably 0.25 to 0.30;

b (for Te) is 0 or from >0 to 1, preferably 0.01 to 0.40, more preferably 0.05 to 0.30, more preferably 0.05 to 0.20, most preferably 0.09 to 0.15;

c (for Nb) is from >0 to 1, preferably 0.01 to 0.40, more preferably 0.05 to 0.30, more preferably 0.10 to 0.25, most preferably 0.14 to 0.20; and n (for O) is a number which is determined by the valency and frequency of elements other than oxygen.

The above-mentioned mixed metal oxide of molybdenum, vanadium, niobium and optionally tellurium may be prepared in many ways. Examples of catalysts comprising such mixed metal oxide and processes for preparing these, are for example disclosed in above-mentioned U.S. Pat. No. 7,091,377, WO2003064035, US20040147393, WO2010096909 and US20100256432, the disclosures of which are herein incorporated by reference.

Suitably, in the present invention, the mixed metal oxide in the above-mentioned component a) crystallizes in a primitive orthorhombic space group. In particular, said mixed metal oxide crystallizes in the primitive orthorhombic space group Pba2. Said space group Pba2 is in so-called Hermann-Mauguin notation and corresponds to the "32" space group in the International Tables for Crystallography, Volume A. "Orthorhombic" refers to a crystal system where the atomic stacking displays a combination of symmetry elements that results in a unit cell shaped as a rectangular cuboid/rectangular parallelepiped/rectangular prism. The lengths of the three independent cell edges typically lie in the following ranges under ambient temperature and pressure: a=21.0-21.3 Å, b=26.5-26.8 Å, c=3.9-4.2 Å.

Suitably, the present catalyst comprises particles comprising the above-mentioned mixed metal oxide of molybdenum, vanadium, niobium and optionally tellurium. Such mixed metal oxide particles may have a crystallite size which is of from 30 to 150 nanometers (nm; $10^{-9}$ meters), preferably of from 50 to 110 nm, more preferably of from 60 to 100 nm, most preferably of from 70 to 90 nm. Preferably, the crystallite size of such mixed metal oxide particles as contained in the catalyst is at least 20 nm, more preferably at least 30 nm, more preferably at least 40 nm, more preferably at least 50 nm, more preferably at least 60 nm, most preferably at least 70 nm. Preferably, the crystallite size of such mixed metal oxide particles as contained in the catalyst is at most 200 nm, more preferably at most 180 nm, more preferably at most 160 nm, more preferably at most 150 nm, more preferably at most 140 nm, more preferably at most 130 nm, more preferably at most 120 nm, more preferably at most 110 nm, more preferably at most 100 nm, most preferably at most 90 nm.

Further, suitably in the present invention, such mixed metal oxide particles as contained in the catalyst comprise mixed metal oxide which crystallizes in a primitive orthorhombic space group, in particular in the primitive orthorhombic space group Pba2, and the crystallite size of such mixed metal oxide ceria particles as contained in the catalyst, as derived from the broadening of the peak in the X-ray diffraction pattern at the (h,k,l) indice mentioned in the table below, may lie in the ranges and may have the minimums and maximums as described above for the (volume-based, average) crystallite size for such mixed metal oxide particles as contained in the catalyst of the present invention.

| (h, k, l)  | 2θ [CuKα] (°) |
|------------|---------------|
| (0, 0, 1)  | 22.1          |

In the present invention, the ratio of the crystallite size of the above-mentioned mixed metal oxide particles to the crystallite size of the ceria particles may be of from 0.1:1 to 10:1, or of from 0.2:1 to 5:1, or of from 0.3:1 to 2:1, or of from 0.4:1 to 1.5:1, or of from 0.5:1 to 1:1. Suitably, said ratio is at least 0.1:1 or at least 0.2:1 or at least 0.3:1 or at least 0.4:1 or at least 0.5:1. Further, suitably, said ratio is at most 10:1 or at most 5:1 or at most 2:1 or at most 1.5:1 or at most 1:1.

In the present invention, the catalyst is a heterogeneous catalyst.

Further, in the present invention, the amount of the ceria particles, based on the total amount of the catalyst, is of from 1 to 60 wt. %, preferably 1 to 40 wt. %, more preferably 5 to 25 wt. %. Said amount of the ceria particles is at least 1 wt. %, and may be at least 3 wt. %, or at least 5 wt. %, or at least 7 wt. %, or at least 10 wt. %. Further, said amount of the ceria particles is at most 60 wt. %, and may be at most 50 wt. %, or at most 40 wt. %, or at most 35 wt. %, or at most 30 wt. %, or at most 25 wt. %.

Still further, in the present invention, the amount of the mixed metal oxide of molybdenum, vanadium, niobium and optionally tellurium may be of from 99 to 40 wt. %, preferably 99 to 60 wt. %, more preferably 95 to 75 wt. %. Said amount of the mixed metal oxide particles may be at least 40 wt. %, or at least 50 wt. %, or at least 60 wt. %, or at least 65 wt. %, or at least 70 wt. %, or at least 75 wt. %. Further, said amount of the mixed metal oxide particles may be at most 99 wt. %, or at most 97 wt. %, or at most 95 wt. %, or at most 93 wt. %, or at most 90 wt. %.

In addition to the above-mentioned ceria particles, the present catalyst may comprise one or more support materials. These one or more support materials may be selected from the group consisting of silica, alumina and silica-alumina. The weight ratio of the above-mentioned ceria particles to said one or more support materials may vary widely and may be of from 0.1:1 to 20:1, suitably of from 0.1:1 to 10:1, more suitably of from 0.5:1 to 5:1.

Further, the present invention relates to a process for preparing a catalyst, preferably the above-described catalyst, which comprises mixing a mixed metal oxide of molybdenum, vanadium, niobium and optionally tellurium with ceria particles having a crystallite size greater than 15 nm, wherein the amount of the ceria particles, based on the total amount of the catalyst, is of from 1 to 60 wt. %. Said mixing step results in a mixture comprising the mixed metal oxide and ceria particles.

The preferences and embodiments in relation to the mixed metal oxide and ceria particles as discussed above in relation to the present catalyst also apply to the mixed metal oxide and ceria particles used in the present catalyst preparation process.

In the above-mentioned mixing step, either a powder, preferably a dry powder, or a suspension, preferably an aqueous suspension, comprising the mixed metal oxide may be mixed with the ceria particles. Further, in said mixing step, either a powder, preferably a dry powder, or a suspension, preferably an aqueous suspension, comprising the ceria particles may be mixed with the mixed metal oxide. Preferably, in said mixing step, a powder, preferably a dry powder, comprising the mixed metal oxide and a powder, preferably a dry powder, comprising the ceria particles are mixed.

Within the present specification, by "dry" in relation to the amount of a liquid, for example water, in the above-mentioned dry powder, it is meant an amount which is at most 10 wt. %, preferably at most 5 wt. %, more preferably at most 3 wt. %, more preferably at most 2 wt. %, more preferably at most 1 wt. %, more preferably at most 5,000 ppmw (parts per million by weight), more preferably at most 1,000 ppmw, more preferably at most 500 ppmw, most preferably at most 100 ppmw of the liquid, based on the amount (i.e. weight) of said powder.

In the catalyst preparation process of the present invention, during the above-mentioned mixing step and/or during any further subsequent step or steps, grinding may be performed. However, it is preferred that during one or more of these steps no grinding is performed. Especially, it is preferred that during the above-mentioned mixing step no grinding is performed. This has the advantage that a grinding step may be omitted.

In the catalyst preparation process of the present invention, the above-mentioned mixing step may be followed by a step comprising subjecting the mixture thus obtained to a temperature in the range of from 150 to 500° C. Preferably, said heat treatment step is carried out in the presence of an oxygen gas containing gas, such as air, and may also be referred to as a calcination step. The temperature during said heat treatment step is of from 150 to 500° C., and may be of from 250 to 400° C., or of from 275 to 375° C.

Further, in the catalyst preparation process of the present invention, the above-mentioned mixing step may be followed by a step comprising shaping the mixture thus obtained. In case the present catalyst preparation process also comprises the above-mentioned heat treatment step, in addition to said shaping step, said shaping step preferably precedes said heat treatment step. Said shaping step may comprise tabletting the mixture (into tablets) or extruding the mixture into shaped bodies having a shape different from tablets. In case said shaping step comprises extrusion, preferably before extruding the mixture, an aqueous suspension comprising the mixed metal oxide and ceria particles is provided which suspension may also contain one or more shaping aids which may promote the formation of a paste, which paste is needed during extrusion. Extruded shaped bodies may have any shape, including hollow cylinders and trilobes.

As an example, the present catalyst preparation process may comprise the following steps:

1) mixing a mixed metal oxide of molybdenum, vanadium, niobium and optionally tellurium with ceria particles having a crystallite size greater than 15 nm, wherein the amount of the ceria particles, based on the total amount of the catalyst, is of from 1 to 60 wt. %;

2) shaping the mixture thus obtained, which shaping may comprise tabletting the mixture or extruding the mixture resulting in tablets or extruded shaped bodies, respectively; and 3) subjecting the tablets or extruded shaped bodies thus obtained to a temperature in the range of from 150 to 500° C.

The invention also relates to a catalyst obtained or obtainable by the above-described catalyst preparation process.

Still further, the present invention relates to a process of the oxidative dehydrogenation of an alkane containing 2 to 6 carbon atoms and/or the oxidation of an alkene containing 2 to 6 carbon atoms, comprising contacting oxygen and the alkane containing 2 to 6 carbon atoms and/or the alkene containing 2 to 6 carbon atoms with the above-described catalyst or the catalyst prepared in accordance with the above-described process.

In the alkane oxidative dehydrogenation process and/or alkene oxidation process of the present invention, 1) oxygen ($O_2$) and 2) an alkane containing 2 to 6 carbon atoms and/or alkene containing 2 to 6 carbon atoms may be fed to a reactor. Said components may be fed to the reactor together or separately. That is to say, one or more feed streams, suitably gas streams, comprising one or more of said 2 components may be fed to the reactor. For example, one feed stream comprising oxygen and the alkane and/or alkene may be fed to the reactor. Alternatively, two or more feed streams, suitably gas streams, may be fed to the reactor, which feed streams may form a combined stream inside the reactor. For example, one feed stream comprising oxygen and another feed stream comprising the alkane and/or alkene may be fed to the reactor separately.

In the process of the present invention, oxygen and the alkane containing 2 to 6 carbon atoms and/or alkene containing 2 to 6 carbon atoms are suitably fed to the reactor in the gas phase.

Preferably, in the present alkane oxidative dehydrogenation process and/or alkene oxidation process, that is to say during contacting the oxygen and the alkane and/or alkene with the catalyst, the temperature is of from 300 to 500° C. More preferably, said temperature is of from 310 to 450° C., more preferably of from 320 to 420° C., most preferably of from 330 to 420° C.

Still further, in the present alkane oxidative dehydrogenation process and/or alkene oxidation process, that is to say during contacting the oxygen and the alkane and/or alkene with the catalyst, typical pressures are 0.1-30 or 0.1-20 bara (i.e. "bar absolute"). Further, preferably, said pressure is of from 0.1 to 15 bara, more preferably of from 1 to 8 bara, most preferably of from 3 to 8 bara.

Preferably, in the alkane oxidative dehydrogenation process of the present invention, the alkane containing 2 to 6 carbon atoms is a linear alkane in which case said alkane may be selected from the group consisting of ethane, propane, butane, pentane and hexane. Further, preferably, said alkane contains 2 to 4 carbon atoms and is selected from the group consisting of ethane, propane and butane. More preferably, said alkane is ethane or propane. Most preferably, said alkane is ethane.

Further, preferably, in the alkene oxidation process of the present invention, the alkene containing 2 to 6 carbon atoms is a linear alkene in which case said alkene may be selected from the group consisting of ethylene, propylene, butene, pentene and hexene. Further, preferably, said alkene contains 2 to 4 carbon atoms and is selected from the group consisting of ethylene, propylene and butene. More preferably, said alkene is ethylene or propylene.

The product of said alkane oxidative dehydrogenation process may comprise the dehydrogenated equivalent of the alkane, that is to say the corresponding alkene. For example, in the case of ethane such product may comprise ethylene, in the case of propane such product may comprise propylene, and so on. Such dehydrogenated equivalent of the alkane is initially formed in said alkane oxidative dehydrogenation process. However, in said same process, said dehydrogenated equivalent may be further oxidized under the same conditions into the corresponding carboxylic acid which may or may not contain one or more unsaturated double carbon-carbon bonds. As mentioned above, it is preferred that the alkane containing 2 to 6 carbon atoms is ethane or propane. In the case of ethane, the product of said alkane oxidative dehydrogenation process may comprise ethylene and/or acetic acid, preferably ethylene. Further, in the case of propane, the product of said alkane oxidative dehydrogenation process may comprise propylene and/or acrylic acid, preferably acrylic acid.

The product of said alkene oxidation process comprises the oxidized equivalent of the alkene. Preferably, said oxidized equivalent of the alkene is the corresponding carboxylic acid. Said carboxylic acid may or may not contain one or more unsaturated double carbon-carbon bonds. As mentioned above, it is preferred that the alkene containing 2 to 6 carbon atoms is ethylene or propylene. In the case of ethylene, the product of said alkene oxidation process may comprise acetic acid. Further, in the case of propylene, the product of said alkene oxidation process may comprise acrylic acid.

In addition to oxygen and the alkane and/or alkene, an inert gas may also be fed. Said inert gas may be selected from the group consisting of the noble gases and nitrogen ($N_2$). Preferably, the inert gas is nitrogen or argon, more preferably nitrogen. Said oxygen is an oxidizing agent, thereby resulting in oxidative dehydrogenation of the alkane and/or oxidation of the alkene. Said oxygen may originate from any source, such as for example air. Ranges for the molar ratio of oxygen to the alkane and/or alkene which are suitable, are of from 0.01 to 1, more suitably 0.05 to 0.5. Said ratio of oxygen to the alkane and/or alkene is the ratio before oxygen and the alkane and/or alkene are contacted with the catalyst. In other words, said ratio of oxygen to the alkane and/or alkene is the ratio of oxygen as fed to the alkane and/or alkene as fed. Obviously, after contact with the catalyst, at least part of the oxygen and alkane and/or alkene gets consumed.

Examples of oxydehydrogenation processes, including process conditions, are for example disclosed in above-mentioned U.S. Pat. No. 7,091,377, WO2003064035, US20040147393, WO2010096909 and US20100256432, the disclosures of which are herein incorporated by reference.

The amount of the catalyst in said process is not essential. Preferably, a catalytically effective amount of the catalyst is used, that is to say an amount sufficient to promote the alkane oxydehydrogenation and/or alkene oxidation reaction.

In general, water is formed during the alkane ODH and/or alkene oxidation reaction(s) that take place in said process, which water may end up in the product stream in addition to the desired product. Water may easily be separated from said product stream, for example by cooling down the product stream from the reaction temperature to a lower temperature, for example room temperature, so that the water condenses and can then be separated from the product stream.

The invention is further illustrated by the following Examples.

Examples (A) Preparation of the Catalyst

A mixed metal oxide catalyst containing molybdenum (Mo), vanadium (V), niobium (Nb) and tellurium (Te) was prepared, for which catalyst the molar ratio of said 4 metals was $Mo_1V_{0.29}Nb_{0.17}Te_{0.12}$.

Two solutions were prepared. Solution 1 was obtained by dissolving 15.8 g of ammonium niobate oxalate and 4.0 g of anhydrous oxalic acid dihydrate in 160 ml of water at room temperature. Solution 2 was prepared by dissolving 35.6 g of ammonium heptamolybdate, 6.9 g of ammonium metavanadate and 5.8 g of telluric acid ($Te(OH)_6$) in 200 ml of water at 70° C. 7.0 g of concentrated nitric acid was then added to solution 2. The 2 solutions were combined which yielded an orange gel-like precipitate. The mixture was spray dried with the aid of a Buchi-290 spray drier.

The dried material was further dried in static air at 120° C. for 16 hours, milled to a fine powder and then calcined in static air at a temperature of 325° C. for 2 hours. After the air calcination, the material was further calcined in a nitrogen ($N_2$) stream at 600° C. for 2 hours.

The resulting mixed metal oxide (MMO) powder was then mixed with silica particles and/or ceria particles in a certain weight ratio of silica and/or ceria particles to MMO powder, as shown in Table 1 below. Said silica particles and ceria particles were mixed as powders. The silica particles were Sipernat 500 LS silica particles. The ceria particles contained ceria which crystallizes in the face-centered cubic space group Fm3̄m. Said space group Fm3̄m is in so-called Hermann-Mauguin notation and corresponds to the "225" space group in the International Tables for Crystallography, Volume A. "Cubic" refers to a crystal system where the atomic stacking displays a combination of internal symmetry elements that results in a cube-shaped unit cell. For $CeO_2$, the cubic cell edge length typically lies in the range 5.2-5.4 Å under ambient temperature and pressure.

Further details on the silica and ceria particles are shown in Table 1 below, including the volume-based, average crystallite size (see also Table 2 below) for the ceria particles used.

TABLE 1

| Catalyst | Large ceria particles | Silica particles | Small ceria particles | Weight ratio [silica + ceria] to MMO |
|---|---|---|---|---|
| Crystallite size $\tau$ ($10^{-9}$ m) | 114-131 | n.d. | 14-15 | n.a. |
| A | yes | no | no | 20:80 |
| B (1) | yes | yes | no | 20:80 |
| C (*) | no | yes | no | 20:80 |
| D (*) | no | no | yes | 20:80 |
| E | yes | no | no | 10:90 |
| F | yes | no | no | 35:65 |
| G | yes | no | no | 50:50 |

(*) = not according to the invention;
n.a. = not applicable;
n.d. = not determined;
MMO = mixed metal oxide;
(1) = weight ratio ceria:silica = 1:1

Figure 1:
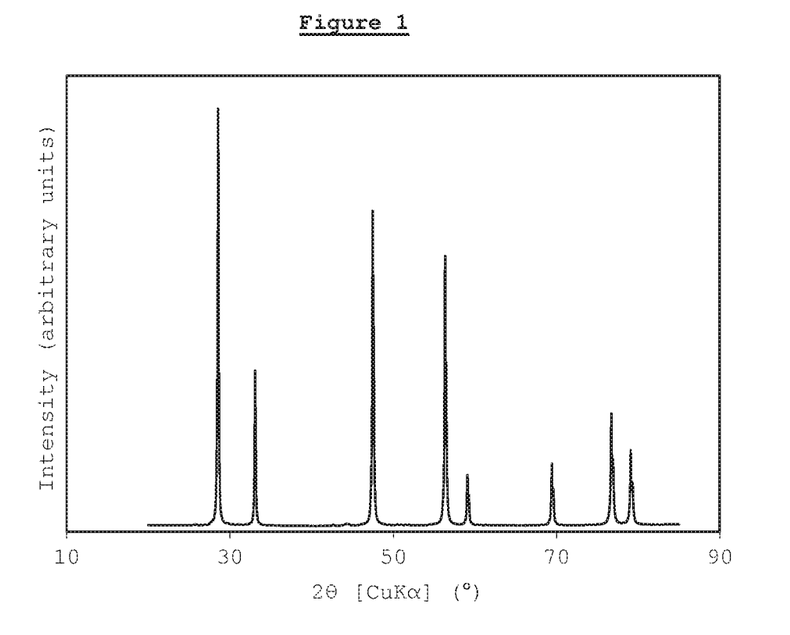
FIG. 1 shows the X-ray diffraction pattern for a powder comprising large ceria particles, as used in the below Examples for catalysts A and B of the invention.
Figure 2:
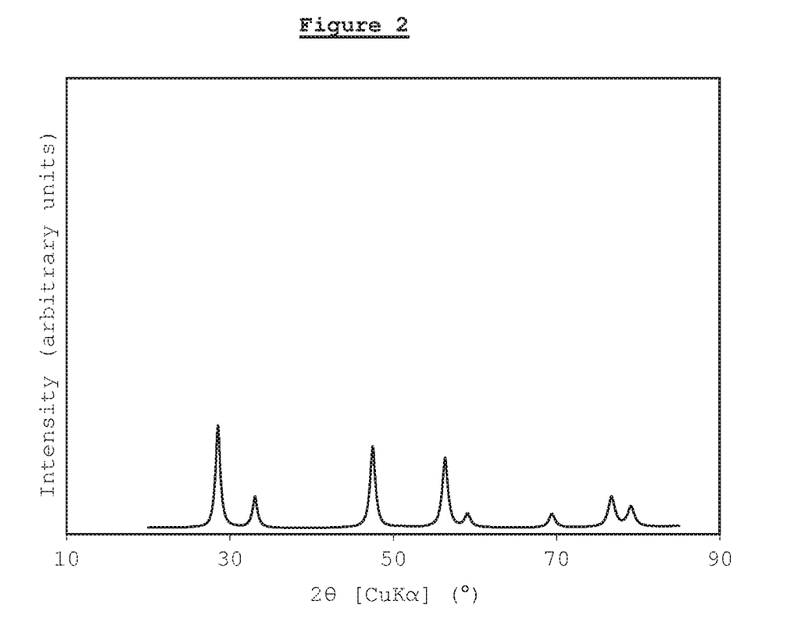
FIG. 2 shows the X-ray diffraction pattern for a powder comprising small ceria particles, as used in the below Examples for comparative catalyst D.

The crystallite sizes mentioned in Tables 1 and 2 concern the crystallite sizes of the ceria particles, as determined by X-ray diffraction, before mixing the ceria particles with the mixed metal oxide powder. The X-ray diffraction patterns for i) the powder comprising the large ceria particles (used for catalysts A, B, E-G of the invention) and ii) the powder comprising the small ceria particles (used for comparative catalyst D) are shown in FIGS. 1 and 2, respectively. Said patterns were measured with constant irradiated area, using CuKα radiation. No other crystalline phases were observed (detection limit was 1% (m/m) for the performed measurements).

The powder comprising the large ceria particles had a purity of 99.9% and is commercially available at Alfa Aesar ("Cerium(IV) oxide Reacton"; lot no. N02B024; CAS no. 1306-38-6). The powder comprising the small ceria particles had a purity of 99.5% and is commercially available at Alfa Aesar ("Cerium(IV) oxide nano powder"; lot no. D06X036; CAS no. 1306-38-3).

All of said (large and small) ceria particles comprised cubic ceria, in particular ceria which crystallizes in the face-centered cubic space group Fm3̄m, and the crystallite size of the ceria particles, as derived from the broadening of the 4 peaks in the X-ray diffraction pattern at the four (h,k,l) indices mentioned in Table 2 below, was greater than 15 nm. All peaks in the 2 diffraction patterns included in FIGS. 1 and 2 can be assigned to said cubic $CeO_2$ (ceria). The vertical axes in FIGS. 1 and 2 are of the same scale, and in said FIGS. 1 and 2 the same units are used for the intensity. The 2 diffraction patterns show a clear difference in reflection broadening. However, the total scattered intensity of a reflection in the pattern of the large ceria particles is approximately equal to that of its counterpart in the pattern of the small ceria particles.

The volume-based, average crystallite sizes T for said large and small cubic ceria particles reported in Table 2 below, are determined from the reflection broadening using the so-called "Scherrer equation" as described above.

TABLE 2

| (h, k, l) | 2θ [CuKα] (°) | $\tau$ of large ceria particles ($10^{-9}$ m) | $\tau$ of small ceria particles ($10^{-9}$ m) |
|---|---|---|---|
| (1, 1, 1) | 28.5 | 114 | 15 |
| (2, 0, 0) | 33.0 | 131 | 14 |
| (2, 2, 0) | 47.4 | 124 | 14 |
| (3, 1, 1) | 56.3 | 120 | 14 |

The data in Table 2 above also indicate that in substantially all directions the crystallite size is substantially the same (substantially isotropic).

The above-mentioned mixed metal oxide powder contained a mixed metal oxide which crystallizes in the primitive orthorhombic space group Pba2. Said space group Pba2 is in so-called Hermann-Mauguin notation and corresponds to the "32" space group in the International Tables for Crystallography, Volume A. "Orthorhombic" refers to a crystal system where the atomic stacking displays a combination of symmetry elements that results in a unit cell shaped as a rectangular cuboid/rectangular parallelepiped/rectangular prism. The lengths of the three independent cell edges typically lie in the following ranges under ambient temperature and pressure: a=21.0-21.3 Å, b=26.5-26.8 Å, c=3.9-4.2 Å. Further, the mixed metal oxide particles contained in said mixed metal oxide powder had a volume-based, average crystallite size of 78 nanometers, as derived from the broadening of the peak in the X-ray diffraction pattern at the (h,k,l) indice mentioned below.

| (h, k, l) | 2θ [cuKa] (°) |
|---|---|
| (0, 0, 1) | 22.1 |

During and after the above-mentioned mixing of the mixed metal oxide powder with silica particles and/or ceria particles, no grinding was performed. After mixing, a mixture of 0.6 wt. % Walocel in water and a suspension of a binding agent were slowly added to the solid mixture in a Retsch mixer. After mixing and compacting, the mixture was extruded into trilobe shaped bodies, followed by a final calcination in static air at a temperature of 325° C. for 2 hours.

The calcined extrudates were then crushed. The crushed material was then sieved using a sieve having a mesh size of 40-80 mesh. The sieved material having a size of 40-80 mesh was then used in the ethane oxidative dehydrogenation experiments described below.

(B) Catalytic Oxidative Dehydrogenation of Ethane

Catalysts A-D were used in experiments involving ethane oxidative dehydrogenation (ethane ODH) within a small-scale testing unit comprising a vertically oriented, cylindrical, quartz reactor having an inner diameter of 2.0 mm. The catalyst was loaded in the reactor. The catalyst bed height was about 6 cm. On top of the catalyst bed, another bed having a height of 8 cm was placed which latter bed contained inert silicon carbide (SiC) particles having a particle size of 0.8 mm.

In these experiments, a gas stream comprising 63 vol. % of ethane, 21 vol. % of oxygen ($O_2$) and 16 vol. % of nitrogen ($N_2$) was fed to the top of the reactor and then sent downwardly through the catalyst bed to the bottom of the reactor. Said gas stream was a combined gas stream comprising a flow of ethane having a rate of 3.00 Nl/hour, a flow of oxygen having a rate of 1.00 Nl/hour and a flow of nitrogen having a rate of 0.77 Nl/hour. "Nl" stands for "normal litre" as measured at standard temperature and pressure, namely 32° F. (0° C.) and 1 bara (100 kPa). The gas hourly space velocity was set to about 4,000 Nl/liter catalyst/hour. The pressure in the reactor was 4.7 bara. The reactor was heated such that the catalyst temperature was about 300° C. This condition was maintained for a number of hours.

Following this initial period at the initial temperature of about 300° C., the temperature was increased stepwise up to at most about 360° C. Further, at each temperature, the conversion was monitored for a number of hours. The conversion of ethane and the product composition were measured with a gas chromatograph (GC) equipped with a thermal conductivity detector (TCD) and with another GC equipped with a flame ionization detector. Acetic acid by-product and water from the reaction were trapped in a quench pot.

Figure 3:
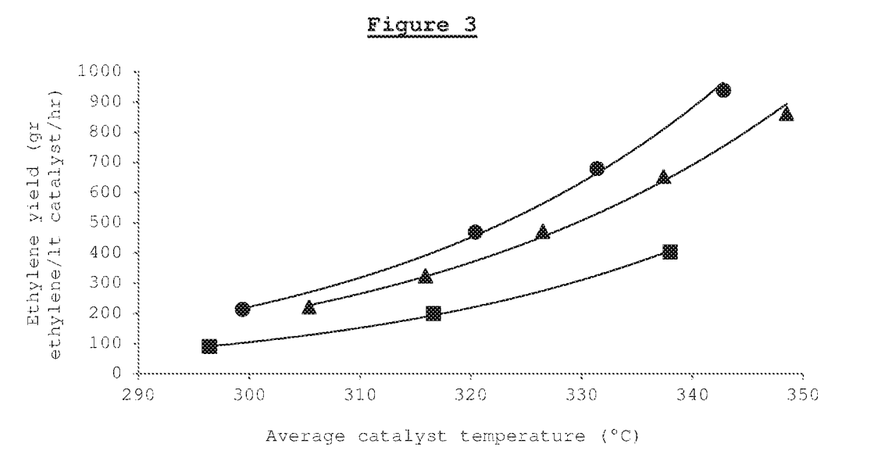
FIG. 3 shows performance data of catalyst A (large ceria particles), catalyst B (silica+large ceria particles) and comparative catalyst C (silica) used in the below Examples.
Figure 4:
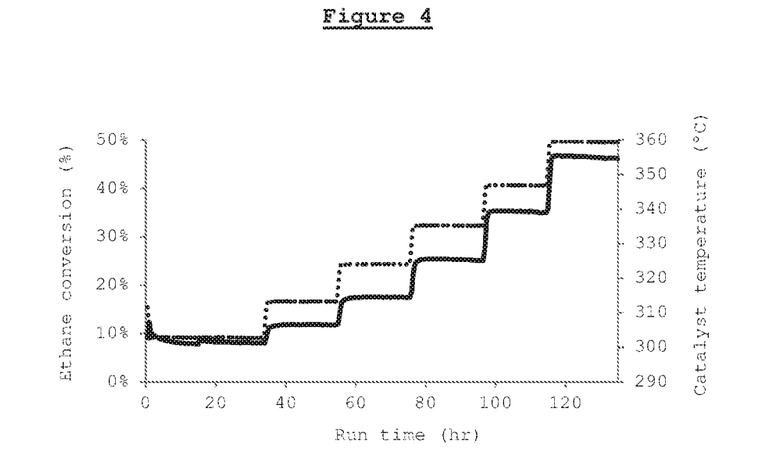
FIG. 4 shows performance data of catalyst A (large ceria particles) used in the below Examples.
Figure 5:
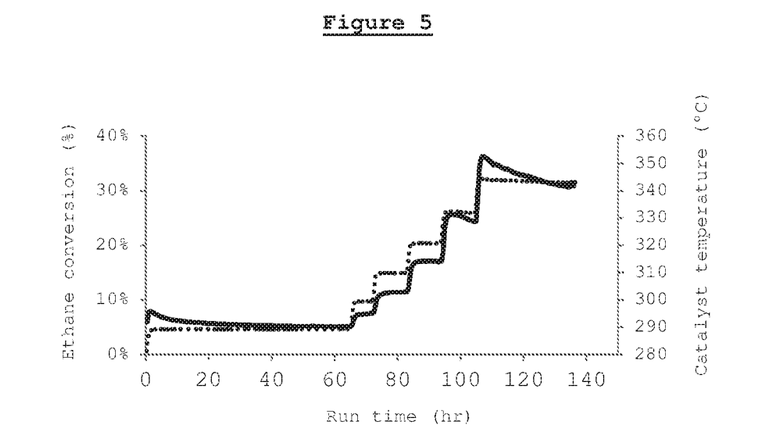
FIG. 5 shows performance data of comparative catalyst D (small ceria particles) used in the below Examples.

The data obtained in the above experiments for Catalysts A, B, C and D are shown in FIGS. 3, 4 and 5.

FIG. 3 shows the performance data of catalysts made with large ceria particles (Catalyst A; line ● in FIG. 3), a mixture of silica and large ceria particles (Catalyst B; line ▲ in FIG. 3) and silica (Catalyst C; line ■ in FIG. 3). In FIG. 3, the catalyst productivity as a function of catalyst temperature is shown. By said catalyst productivity, reference is made to space-time yield which was measured as grams of ethylene produced per liter of catalyst per hour. Further, by said catalyst temperature, reference is made to the average of the top catalyst temperature and the bottom catalyst temperature, wherein the top catalyst temperature is the temperature measured in the catalyst bed at a position which is about 0.5 cm from the top and the bottom catalyst temperature is the temperature measured in the catalyst bed at a position which is about 0.5 cm from the bottom.

Surprisingly, it appears from the data in FIG. 3 that the catalyst productivity is highest when no silica is used but large ceria particles are used in accordance with the invention (compare Catalysts A and B of the invention with (comparative) Catalyst C), and that by increasing the relative amount of said large ceria particles said productivity is further increased (compare Catalyst A with Catalyst B).

FIG. 4 shows the performance data of a catalyst made with large ceria particles (Catalyst A), whereas FIG. 5 shows the performance data of a catalyst made with small ceria particles (Catalyst D). In FIGS. 4 and 5, the ethane conversion (solid line) as a function of time at various catalyst temperatures (dot line) is shown. In the experiments of FIG. 4, the catalyst temperature (dot line) was maintained at about 300° C., about 310° C., about 325° C., about 335° C., about 345° C. and about 360° C. in 6 subsequent time periods, respectively. In the experiments of FIG. 5, the catalyst temperature (dot line) was maintained at about 290° C., about 300° C., about 310° C., about 320° C., about 330° C. and about 345° C. in 6 subsequent time periods, respectively. The solid lines represent the ethane conversion in said time periods.

Surprisingly, it appears from the data in FIGS. 4 and 5 that the catalyst made with large ceria particles is more stable as a function of time than the catalyst made with small ceria particles. For example, if one compares the ethane conversion for Catalysts A and D at a catalyst temperature of about 345° C., one can see that the conversion for Catalyst A of the invention remains stable at about 35%, whereas for (comparative) Catalyst D the conversion is not stable as it decreases over time from about 35% to about 30%.

In another set of ethane ODH experiments, Catalysts E-G were tested within a small-scale testing unit comprising a vertically oriented, cylindrical, steel reactor having an inner diameter of 4.5 mm. The catalyst was loaded in the reactor. A catalyst intake of 0.7 g was used resulting in a bed height of approximately 4 cm.

In these experiments using Catalysts E-G, a gas stream comprising 35 vol. % of ethane, 12 vol. % of oxygen ($O_2$) and 53 vol. % of nitrogen ($N_2$), having a rate of 1.56 Nl/hour, was fed to the top of the reactor and then sent downwardly through the catalyst bed to the bottom of the reactor. The pressure in the reactor was 1.1 bara. The reactor was heated such that the catalyst temperature was about 360° C. This condition was maintained for at least 60 hours at which the ethane conversion was determined.

Table 3 below shows the ethane conversion after 60 run hours. In addition, Table 3 shows the relative activity normalized to the intake of mixed metal oxide (MMO). Although the resulting catalyst activity shows an optimum close to 10 wt. % of ceria (Catalyst E), Table 3 also shows that the relative activity normalized to the intake of MMO increases with increasing ceria content (Catalysts F and G).

TABLE 3

| Catalyst | Ethane conversion | Relative activity (normalized to MMO content) |
| --- | --- | --- |
| E | 33% | 115% |
| F | 29% | 139% |
| G | 25% | 156% |

That which is claimed is:
1. A catalyst comprising:
a) a mixed metal oxide of molybdenum, vanadium, niobium and optionally tellurium; and
b) ceria particles having a volume-based, average crystallite size greater than 30 nanometers (nm);
wherein the amount of the ceria particles, based on the total amount of the catalyst, is from 1 to 60 wt. %,
wherein the ceria particles comprise cubic ceria which crystallizes in the face-centered cubic space group Fm$\bar{3}$m, and the volume-based, average crystallite size of the ceria particles, as derived from the broadening of the 4 peaks in the X-ray diffraction pattern at the four (h,k,l) indices mentioned in the table below, is greater than 30 nm:

| (h, k, l) |
| --- |
| (1, 1, 1) |
| (2, 0, 0) |
| (2, 2, 0) |
| (3, 1, 1). |

2. The catalyst of claim 1, wherein the volume-based, average crystallite size of the ceria particles is from greater than 30 nm to 1,000 nm.

3. The catalyst of claim 1, wherein the amount of the ceria particles, based on the total amount of the catalyst, is from 1 to 40 wt. %.

4. A process for preparing the catalyst of claim 1, which comprises mixing a) and b).

5. The process of claim 4, wherein the crystallite size of the ceria particles is from greater than 30 nm to 1,000 nm.

6. The process of claim 4, wherein the amount of the ceria particles, based on the total amount of the catalyst, is from 1 to 40 wt. %.

7. A process for the oxidative dehydrogenation of an alkane containing 2 to 6 carbon atoms and/or the oxidation of an alkene containing 2 to 6 carbon atoms, comprising contacting oxygen and the alkane containing 2 to 6 carbon atoms and/or the alkene containing 2 to 6 carbon atoms with the catalyst of claim 1.

8. A process for the oxidative dehydrogenation of an alkane containing 2 to 6 carbon atoms and/or the oxidation of an alkene containing 2 to 6 carbon atoms, comprising contacting oxygen and the alkane containing 2 to 6 carbon atoms and/or the alkene containing 2 to 6 carbon atoms with catalyst prepared in accordance with the process of claim 4.

\* \* \* \* \*